United States Patent [19]

Tanabe et al.

[11] Patent Number: 5,391,777
[45] Date of Patent: Feb. 21, 1995

[54] ISOLATION OF STEROIDS CONTAINING A 5,7-DIENE FUNCTIONALITY FROM A STEROL MIXTURE

[75] Inventors: Masato Tanabe, Palo Alto; John G. Johansson, Menlo Park; Dennis Yasuda, Campbell, all of Calif.

[73] Assignee: SRI International, Menlo Park, Calif.

[21] Appl. No.: 152,259

[22] Filed: Nov. 12, 1993

Related U.S. Application Data

[63] Continuation of Ser. No. 869,574, Apr. 15, 1992, abandoned.

[51] Int. Cl.$^6$ .............................................. C07J 75/00
[52] U.S. Cl. .................................. 552/545; 552/540; 552/541
[58] Field of Search ........................ 552/540, 541, 545

[56] References Cited

U.S. PATENT DOCUMENTS

| | | |
|---|---|---|
| 4,011,250 | 3/1977 | Ishikawa et al. |
| 4,069,321 | 1/1978 | Jones et al. |
| 4,148,810 | 4/1979 | Strewe .......................... 552/545 |
| 4,271,288 | 6/1981 | Woo . |
| 4,298,539 | 11/1981 | Koskenniska ............... 260/397.25 |
| 4,849,112 | 7/1989 | Barder et al. ..................... 552/545 |
| 5,252,729 | 10/1993 | DeCrosta et al. ................ 552/545 |
| 5,264,599 | 11/1993 | Hammond et al. ............... 552/545 |
| 5,304,547 | 4/1994 | Mentink et al. .................. 552/545 |

FOREIGN PATENT DOCUMENTS

| | | |
|---|---|---|
| 000073 | 12/1978 | European Pat. Off. . |
| 337305 | 10/1989 | European Pat. Off. . |
| 2327790 | 5/1977 | France . |
| 2384755 | 10/1978 | France . |
| 2535308 | 2/1976 | Germany . |

OTHER PUBLICATIONS

D. R. Crump et al., "(22S)-Hydroxyvitamin D$_4$" *J.C.S. Perkins Trans. I*, pp. 2731–2733 (1973).

S. C. Eyley et al., "Synthesis of 25-Hydroxyprovitamin D$_3$ and 25ξ,26-dihydroxyprovitamin D$_3$", *J.C.S. Perkins Trans. I*, pp. 731–735 (1976).

A. M. Moiseenkov et al., "Partial synthesis of 25-hydroxycholesterol and 25-hydroxyprovitamin D$_3$ *using a cyclopropyl carbinyl rearrangement*"*Bioorg. Khim.* 9(1):118–122 (1983).

G. M. Segal et al., "Synthesis of (Z)-17(20)-dehydrocholesterol and 25-hydrosyprovitamin d$_3$. A new method for the stereospecific construction of sterol side chains" *Bioorg. Khim.* 7(3):429–435 (1981).

Stoilov et al., "Biosynthetic studies of marine lipids 12. Biosynthesis in marine sponges of sterols possesing the delta-5,7-nucleus typical of fungi and the 24-alkyl side chain characteristic of plants", *Tetrahedron* 43(10):2213–2222 (1987).

Barton et al., "The partial synthesis of ergosta-5,7-2-2-24(28)-tetraen-3-beta-ol", *J. Chem. Soc., Chem. Commun.*, No. 15:939–940 (1970).

Barton et al., "Biosynthesis of terpenes and steriods. Part V. The partial synthesis of ergosta-5,7-22-24(2-8)-tetraen-3-beta-ol, a biosynthetic precursors or ergosterol", *J. Chem. Soc. (C), Perkin Transactions 1*: 1968–1974 (1971).

(List continued on next page.)

*Primary Examiner*—Johann Richter
*Assistant Examiner*—Kimberly J. Kestler
*Attorney, Agent, or Firm*—Dianne E. Reed

[57] ABSTRACT

A method is provided for isolating 5,7-diene-containing steroids, particularly 3β-ols and esters of 3β-ols, from a sterol mixture. The method involves (1) treating the mixture with a dienophile or with an oxidizable dienophile precursor in combination with an oxidizing agent so as to provide a Diels-Alder adduct of the 5,7-diene to be isolated, followed by (2) removal of the adduct from the mixture and (3) regeneration of the 5,7-diene with a suitable reducing agent. The invention also encompasses subsequent purification steps and intermediate modification of the Diels-Alder intermediate, e.g., wherein chemical conversion of the Diels-Alder adduct is effected prior to regeneration of the 5,7-diene. Novel compounds which are Diels-Alder adducts of 5,7-diene-containing steroids are provided as well.

24 Claims, No Drawings

OTHER PUBLICATIONS

Barton et al., "Biosynthesis of terpenes and steroids. Part IX. The sterols of some mutant yeasts and their relationship to the biosynthesis of ergosterol", *J. Chem. Soc. (C), Perkin Transactions* 1, No. 11: 1326–1333 (1974).

Yang et al., "Synthesis of 24-dehydrocholecalciferol", *Steroids* 35(3):329–334 (1980).

Shul'man et al., "Synthesis of hydroxylated group D provitamin derivatives" *J. Gen. Chem USSR* 58(1):191–198 (1988).

Shakhova et al., "Structure of the product of the Jones chromium trioxide oxidation of the 1,4-phthalazine-dione-7-dehydrocholesterol adduct", *J. Gen. Chem USSR* 46(7):1598–1600 (1976).

ISOLATION OF STEROIDS CONTAINING A 5,7-DIENE FUNCTIONALITY FROM A STEROL MIXTURE

This application is a continuation of application Ser. No. 07/869,574, filed Apr. 15, 1992, now abandoned.

TECHNICAL FIELD

This invention relates generally to synthetic methods involving steroids, and more particularly relates to a novel method for isolating steroids containing a 5,7-diene functionality from a mixture of sterols. The method is especially useful for isolating 5,7-diene-containing sterols from a mixture containing yeast sterol metabolites.

BACKGROUND

The present invention derives from the development of a biotechnological fermentation process that produces a yeast sterol mixture enriched in cholesta-5,7,24-trienol-3$\beta$-ol and accompanied by other di-olefinic yeast sterol metabolites. The aforementioned trienol, having the chemical structure (I),

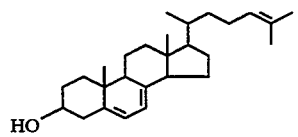

(I)

is a valuable compound useful, inter alia, as an intermediate in the synthesis of a variety of compounds related to vitamin $D_3$ derivatives, e.g., cholesta-5,7-diene-3$\beta$-25-diol and other 25-substituted vitamin $D_3$ precursors. Accordingly, it is necessary to provide a feasible process for isolating and purifying the trienol (I) from a fermentation mixture containing yeast sterol metabolites, including lanosterol, 4,4-dimethylzymosterol, 4-methylzymosterol, zymosterol and cholesta-7,24-diene-3$\beta$-ol. The mixture may also include squalene. As may be seen from the following structures, a number of these compounds containing two or more degrees of unsaturation. Thus, the process of isolation and separation must be specific.

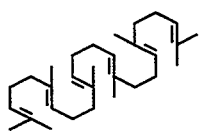

SQUALENE
(II)

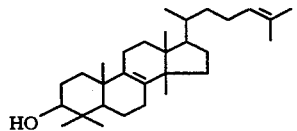

LANOSTEROL
(III)

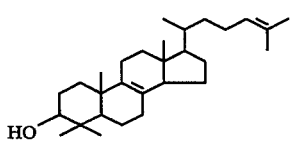

4,4-DIMETHYLZYMOSTEROL
(IV)

-continued

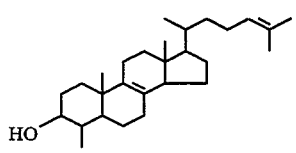

4-METHYLZYMOSTEROL
(V)

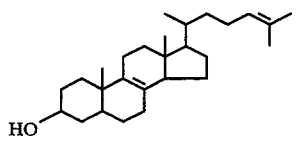

ZYMOSTEROL
(VI)

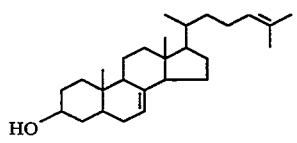

CHOLESTA-7,24-DIENE-3-OL
(VII)

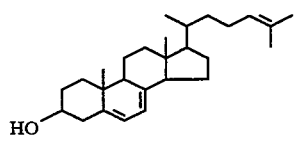

CHOLESTA-5,7,24-TRIENE-3-OL
(VIII)

S.C. Eyley et al., *J. C. S. Perkins Trans. I*, pp. 731–735 (1976), describe a method for synthesizing 25-hydroxyprovitamin $D_3$ and 25$\xi$,26-dihydroxyprovitamin $D_3$. The method involves initial reaction of the C-22 aldehyde derived by degradation of ergosterol with a Grignard reagent derived from 4-chloro-2-methylbut-1-ene, followed by reductive elimination of the mesylate of the resulting C-22 alcohol.

J. P. Moreau et al., *J. Org. Chem.* 39(14):2018–2023 (1974), is a background reference which describes the synthesis of 5$\alpha$-cholesta-7,24-dien-3$\beta$-ol and cholesta-5,7,24-trien-3$\beta$-ol.

J. W. Blunt et al., *Biochemistry* 8(2):671–675 (February 1969), describe methods of synthesizing cholesta-5,7-diene-3$\beta$,25-diol, followed by conversion to 25-hydroxycholecaliferol.

S. S. Yang et al., *Tetrahedron Letters* 27:2315–2316 (1977), is a background reference describing a method for synthesizing 25-fluorovitamin $D_3$.

D. R. Crump et al., *J. C. S. Perkins Trans. I*, pp. 2731–2733 (1973), describes a method for synthesizing (22S)-hydroxyvitamin $D_4$ using ergosterol acetate as a starting material. The synthesis involves selective epoxidation of the 22,23-double bond of ergosterol acetate, followed by a Grignard reaction on the hexanor-22-aldehyde, and irradiation.

SUMMARY OF THE INVENTION

Accordingly, it is a primary object of the invention to provide a method for isolating and removing a 5,7-diene-containing steroids, particularly 3$\beta$-ols and esters of 3$\beta$-ols, from a mixture of sterols.

It is another object of the invention to provide such a method wherein the mixture of sterols comprises a plurality of yeast sterol metabolites.

It is still another object of the invention to provide such a method wherein the plurality of yeast sterol metabolites includes squalene, lanosterol, 4,4-dimethylzymosterol, 4-methylzymosterol, zymosterol and cholesta-7,24-diene-3β-ol.

It is yet another object of the invention to provide such a method wherein the 5,7-diene-containing steroid is cholesta-5,7,24-triene-3β-ol.

It is a further object of the invention to provide such a method which involves treating the mixture with a dienophile as will be described in detail herein.

It is still a further object of the invention to provide such a method which involves treating the mixture with a oxidizable dienophile precursor, and with an oxidizing agent capable of oxidizing the dienophile precursor to a dienophile.

It is yet a further object of the invention to provide such a method which enables preparation of the isolated 5,7-diene-containing steroids in purified form.

It is still a further object of the invention to provide novel compounds which are selected Diels-Alder adducts of 5,7-diene-containing steroids as will be described in detail herein.

Additional objects, advantages and novel features of the invention will be set forth in part in the description which follows, and in part will become apparent to those skilled in the art upon examination of the following, or may be learned by practice of the invention.

In one aspect, the invention is a method of isolating asteroid, typically a 3β-ol or an ester of a 3β-ol, containing a 5,7-diene functionality from a mixture of sterols, wherein the method involves: (a) treating the mixture with a dienophile having the structural formula X—R=R—Y, in which the R's are both N or both C—Q where the Q's are H or together form a third bond, and wherein X and Y are electron-withdrawing groups which may or may not be linked together; (b) removing the Diels-Alder adduct so formed from the mixture; and (c) treating the Diels-Alder adduct with a reducing agent which is effective to cleave the adduct and regenerate the 5,7-diene-containing steroid.

In another aspect, the invention is a method of isolating asteroid containing a 5,7-diene functionality from a mixture of sterols, wherein the method involves: (a) treating the mixture with (i) an oxidizable dienophile precursor having the structural formula X—NH—NH—Y where X and Y are as above, and (ii) an oxidizing agent effective to oxidize the precursor; (b) removing the Diels-Alder adduct so formed from the mixture; and (c) treating the Diels-Alder adduct with a reducing agent which is effective to cleave the adduct and regenerate the 5,7-diene-containing steroid.

In either case, the isolated 5,7-diene-containing steroid can then be purified via crystallization, chromatography, precipitation, or the like.

In still another aspect of the invention, modification of the Diels-Alder adduct is carried out between steps (a) and (b), typically a modification which could not be made with the reactive 5,7-diene functionality present.

In still another aspect of the invention, novel compounds are provided in the form of Diels-Alder adducts of certain 5,7-diene-containing steroids.

DETAILED DESCRIPTION OF THE INVENTION

Before the present methods are disclosed and described, it is to be understood that this invention is not limited to the isolation and purification of specific 5,7-diene-containing steroids, to the treatment of specific sterol mixtures, or to the use of specific synthetic reagents, i.e., dienophiles, oxidizing agents, reducing agents, or the like, as such may, of course, vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "a sterol" includes mixtures of sterols, reference to "asteroid" includes mixtures of two or more steroids, and the like.

In this specification and in the claims which follow reference will be made to a number of terms which shall be defined to have the following meanings:

"Alkyl" refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred "alkyl" groups herein contain 1 to 12 carbon atoms. "Lower alkyl" refers to an alkyl group of 1 to 6, more preferably 1 to 4, carbon atoms.

"Alkylene" refers to a difunctional saturated branched or unbranched hydrocarbon chain containing from 1 to 24 carbon atoms, and includes, for example, methylene ($-CH_2-$), ethylene ($-CH_2-CH_2-$), propylene ($-CH_2-CH_2-CH_2-$), 2-methylpropylene [$-CH_2-CH(CH_3)-CH_2-$], hexylene [$-(CH_2)_6-$] and the like. "Lower alkylene" refers to an alkylene group of 1 to 6, more preferably 1 to 4, carbon atoms.

"Alkenylene" refers to a difunctional branched or unbranched hydrocarbon chain containing from 2 to 24 carbon atoms and at least one double bond. "Lower alkenylene" refers to an alkenylene group of 2 to 6, more preferably 2 to 5, carbon atoms.

"Alkynyl" refers to a branched or unbranched acetylenically unsaturated hydrocarbon group of 2 to 24 carbon atoms such as ethynyl, 1-propynyl, 2-propynyl, 1-butynyl, 2-butynyl, octynyl, decynyl, tetradecenyl, hexadecynyl, and the like. "Lower alkynyl" refers to an alkynyl group of 2 to 6, more preferably 2 to 4, carbon atoms.

"Acyl" refers to a group of the structure $-(C=O)-R'$, where R' is as described herein. Acyl, therefore, includes such groups as, for example, acetyl, propanoyl (or propionyl), isopropanoyl, n-butanoyl (or n-butyryl), benzoyl, phenylacetyl, and the like. "Lower acyl" refers to an acyl group wherein R' is lower alkyl as defined above.

"Aryl" refers to a phenyl or 1- or 2-naphthyl group. "Monocyclic aryl" refers to a phenyl group. Optionally, these groups are substituted with up to five ring substituents selected from the group consisting of $-(CH_2)_n-NH_2$, $-(CH_2)_n-COOH$, $-NO_2$, halogen and lower alkyl, where n is an integer in the range of 0 to 6 inclusive.

"Arylene" refers to a difunctional aromatic moiety; "monocyclic arylene" refers to a phenylene group. These groups may be substituted with up to four ring substituents selected from the group consisting of —(CH$_2$)$_n$—NH$_2$, —(CH$_2$)$_n$—COOH, —NO$_2$, halogen and lower alkyl, where n is an integer in the range of 0 to 6 inclusive.

"Halo" or "halogen" refers to fluoro, chloro, bromo or iodo, usually regarding halo substitution for a hydrogen atom in an organic compound. Of the halos, chloro and bromo are generally preferred with chloro generally being the more preferred.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

In describing the location of groups and substituents, the following numbering system will be employed.

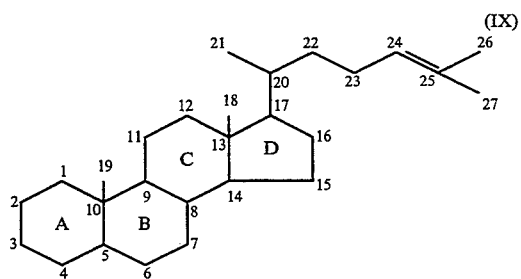

This system is intended to conform the numbering of the cyclopentanophenanthrene nucleus to the convention used by the IUPAC or Chemical Abstracts Service. The term "steroid" as used herein is intended to mean compounds having the aforementioned cyclopentanophenanthrene nucleus.

The symbols "α" and "β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn. In the present disclosure, if bonds are not indicated explicitly as "α" or "β", it should be assumed that the structural formula encompasses both types of compounds, with the stereochemical configuration of the naturally occurring steroid molecule preferred.

In addition, the five- or six-membered rings of the steroid molecule are often designated A, B, C and D as shown.

The term "sterol" as used herein is intended to mean asteroid molecule having the backbone structure illustrated above, and containing at least one hydroxyl group. Generally, the sterols of the present invention have a single hydroxyl group at the 3-position.

The term "purified compound" as used herein intends a composition which contains at least about 80 wt. % of that compound, preferably at least about 90 wt. %, and most preferably at least about 99 wt. %.

The 5,7-diene-containing steroids which may be isolated and purified using the present technique have the general structural formula

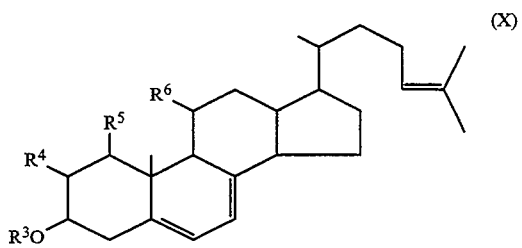

wherein R$^3$ is selected from the group consisting of H and R'CO— where R' is lower alkyl or monocyclic aryl of 5 to 7 carbon atoms, and R$^4$, R$^5$ and R$^6$ are independently selected from the group consisting of H, hydroxyl and lower alkyl. The R$^3$ moiety, if other than H, is thus a hydroxyl-protecting group; typical R$^3$ moieties are H, CH$_3$CO— and C$_6$H$_5$CO—. If R$^4$, R$^5$ and R$^6$ are other than H and OH, they will generally be methyl or ethyl, more typically methyl.

As noted earlier, the method of the present invention is particularly useful for isolating and purifying cholesta-5,7,24-triene-3β-ol from a mixture of sterols, e.g., a mixture of yeast sterol metabolites (squalene, lanosterol, 4,4-dimethylzymosterol, and the like). Virtually any sterol may be present in the mixture so long as the compounds do not contain a conjugated diene functionality. As illustrated by the yeast sterol metabolite mixture shown above, the compounds present in the composition from which the 5,7-diene-containing sterol is to be isolated may contain two or more degrees of unsaturation.

In a first embodiment of the invention, the mixture of sterols is treated with a dienophile having the structural formula X—R=R—Y wherein the R's are both N or both C—Q where the Q's are H or together form a third bond. Thus, the dienophile in this embodiment will have the structure X—N=N—Y, X—(CQ)=(CQ)—Y, or X—C≡C—Y. This type of reaction will sometimes be referred to herein as reaction type (1). The substituents X and Y are electron-withdrawing groups which are independently selected from the group consisting of —COOH, —CHO, —NO$_2$, —CN, —COOR$^1$ and —COR$^1$ where R$^1$ is lower alkyl, or X and Y may be linked together to form a —(CO)—Z—(CO)— bridge. In the latter case, i.e., when X and Y are linked together, the "Z" linkage is lower alkylene, lower alkenylene, monocyclic arylene of 5 to 7 carbon atoms with up to 4 ring substituents, —S—, or —NR$^2$— wherein R$^2$ is H, lower alkyl or monocyclic aryl of 5 to 7 carbon atoms with up to 5 ring substituents. Ring substituents are selected from the group consisting of —(CO$_2$)$_2$—NH$_2$, —(CH$_2$)$_n$—COOH, —NO$_2$, halogen and lower alkyl, wherein n is an integer in the range of 0 to 6 inclusive. Dienophiles within the aforementioned group may be available commercially or may be readily synthesized using starting materials and techniques known to those skilled in the art of synthetic organic chemistry. Examples of particular dienophiles useful herein include the following:

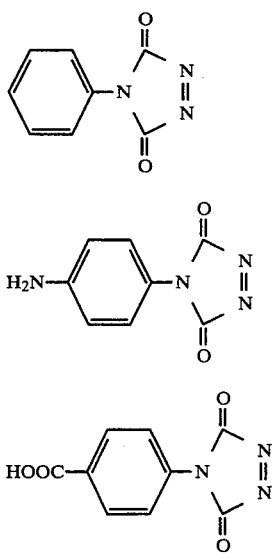

(XI)

(XII)

(XIII)

These dienophiles are available commercially from a number of sources, e.g., from the Aldrich Chemical Company, Milwaukee, Wis. As will be appreciated by those skilled in the art, such dienophiles may also be readily synthesized using conventional techniques (see, e.g., S. W. Moje and P. Beak, *J. Org. Chem.* 39(20):2951 (1974), and K. Rufenacht, *Helv. Chim. Acta* 51:518 (1968)).

In a second embodiment, a dienophile precursor is used which may be converted to a dienophile with a suitable oxidizing agent. This reaction will sometimes be referred to herein as reaction (2). Here, the sterol mixture is simultaneously treated with the dienophile precursor and with an oxidizing agent effective to oxidize the precursor to an active dienophile. The dienophile precursor has the structural formula X—NH—NH—Y wherein X and Y are as defined above. Exemplary dienophile precursors are wherein X and Y are linked together to form a —(CO)—Z—(CO)— bridge, with Z as defined above. Preferably, in this embodiment, Z is monocyclic arylene of 5 to 7 carbon atoms substituted with up to 2 substituents selected from the group consisting of —(CH$_2$)$_n$—NH$_2$ and —(CH$_2$)$_n$—COOH, wherein n is an integer in the range of 0 to 6 inclusive. Dienophile precursors within the aforementioned group may be available commercially or may be readily synthesized using starting materials and techniques known to those skilled in the art of synthetic organic chemistry (see, e.g., H. D. K. Drew and H. H. Hatt, *J. Chem. Soc.* 16 (1937)). Examples of particular dienophile precursors useful herein (again, such compounds are available commercially, or may be readily synthesized) include the following:

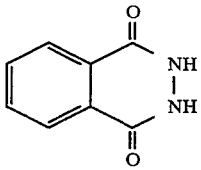

(XIV)

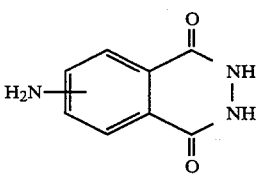

(XV)

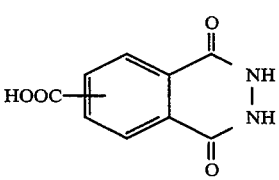

(XVI)

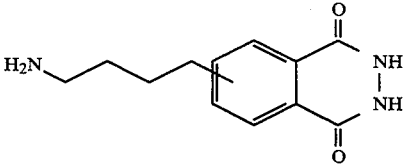

(XVII)

and (XIV)

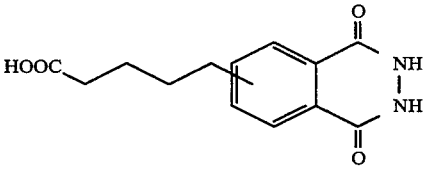

(XVIII)

Any oxidizing agent capable of oxidizing the dienophile precursor to an active dienophile may be used, with the exception of oxidizing agents which could interfere with the formation of the Diels-Alder adduct or which could interact detrimentally in some other way with any of the sterols in the sterol mixture. Exemplary oxidizing agents include potassium peroxymonosulfate, lead tetraacetate, iodosobenzene diacetate, N-bromosuccinimide and t-butyl hypochlorite.

Either of the aforementioned reactions, i.e., treatment of the sterol mixture with a dienophile having the structure X—R=R—Y, or with a dienophile precursor of the structure X—NH—NH—Y and an oxidizing agent, results in the formation of a Diels-Alder adduct. These reactions are illustrated in the following schemes:

Reaction (1)

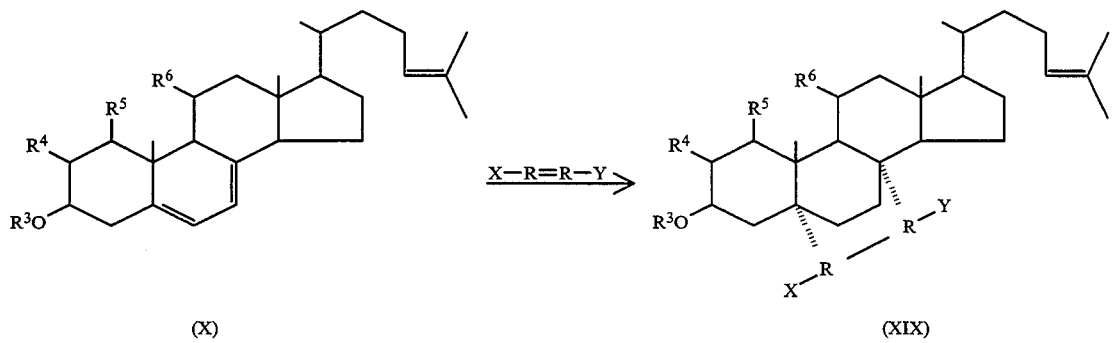

(X)                                    (XIX)

Reaction (2)

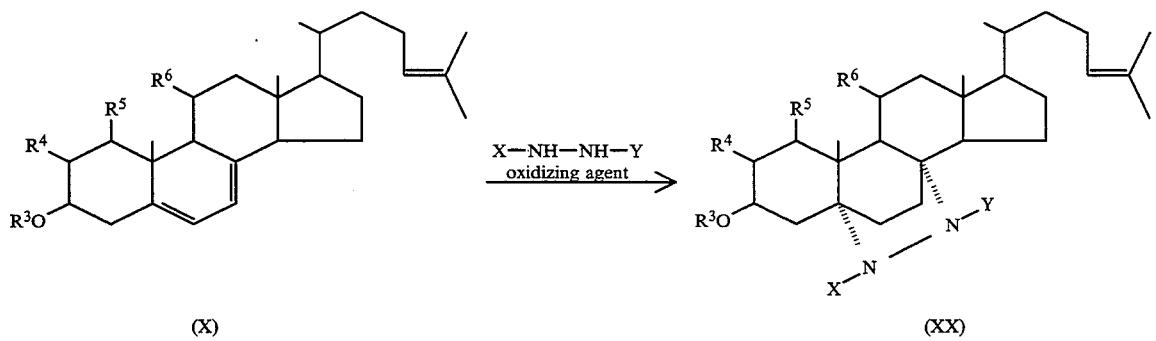

(X)                                    (XX)

Both types of reactions are carried out in an inert atmosphere, in a non-reactive, preferably polar organic solvent effective to dissolve the reactants. With reaction (2), it is preferred that the oxidizing agent be added gradually to a solution of the steroid and the dienophile in the selected solvent, and that the procedure be carried out at a relatively low temperature, i.e., 10° C. or lower (0° C. to 5° C., as may be obtained by an ice/water bath, is optimal). At least about 15 minutes, preferably at least 1 hour, should be allowed for the reaction to occur.

After preparation of the Diels-Alder adduct using either reaction (1) or reaction (2), the adduct is removed from the reaction mixture and regenerated to give the 5,7-diene-containing steroid in isolated form. Removal of the adduct from the reaction mixture is preferably done chromatographically, using, for example, a silica gel column which will preferentially bind the Diels-Alder adduct. The chemical and physical properties of the Diels-Alder adduct can be varied by manipulating the substituents present on the dienophile as well as by varying $R^3$. For example, basic properties can be imparted to the Diels-Alder adduct by the use of a dienophile containing a basic substituent, e.g., —NH₂, —(CH₂)ₙ—NH₂, or the like. The adduct is then a basic molecule and separable from the sterol mixture using acid extraction. Similarly, acidic properties can be imparted to the Diels-Alder adduct by the use of a dienophile containing an acid substituent, e.g., —COOH, —(CH₂)ₙ—COOH, or the like. The adduct will then be an acidic molecule and separable from the sterol mixture using basic extraction.

Also, as alluded to above, after preparation of the Diels-Alder adduct, the moiety present at $R^3$ may be converted to a functionality which imparts desirable crystallization and/or precipitation parameters. For example, a hydroxyl group present at C-3 may be readily converted to a benzoate species, which in turn will make the adduct more crystalline and more readily separable from the sterol mixture.

Regeneration of the 5,7-diene-containing steroid is then accomplished by treatment of the adduct with a reducing agent such as lithium aluminum hydride ("LAH"), diisobutyl aluminum hydride ("DiBAL"), Red-Al® (a solution of sodium bis(2-methoxy-ethoxy)aluminum hydride in toluene, available from the Aldrich Chemical Company, Inc., Milwaukee, Wis.), or the like. Lithium aluminum hydride is particularly preferred. The reaction proceeds initially at a low temperature, i.e., 10° C. or lower (again, as may be obtained by an ice/water bath), followed by, after at least about 30 minutes, warming to at least about 50° C. for at least several minutes. Excess reducing agent and any salts or derivatives thereof are then removed, e.g., by filtration through celite or the like. Evaporation of the reaction mixture will then give rise to the 5,7-diene-containing steroid.

Purification of the regenerated 5,7-diene-containing steroid may then be carried out using any of a number of techniques which will be readily appreciated by those of ordinary skill in the art. For example, purification can be effected via recrystallization e.g., using methanol, ethanol, or the like, or using precipitation or chromatographic techniques.

Where the 5,7-diene-containing steroid is cholesta-5,7,24-triene-3β-ol, the isolated, purified material may be used to prepare cholesta-5,7-diene-3β,25-diol as described in commonly assigned U.S. patent application Ser. No. 07/869,328, now abandoned entitled "Method of Preparing Cholesta-5,7-Diene-3,25-Diol and Analogs Thereof", inventors J. Johansson et al., filed on even date herewith. The disclosure of that patent application is hereby incorporated by reference in its entirety. Cholesta-5,7-diene-3β,25-diol is a biologically important hydroxylated pro-vitamin D₃ metabolite which may be converted by sunlight or other well-established photochemical methods to 25-hydroxy vitamin $D_3$. Such vitamin $D_3$ derivatives are useful in a number of contexts, e.g., in topical pharmaceutical formulations (for the treatment of skin disorders or the like), in oral vitamin compositions, and as livestock feed additives.

In a variation on the above-described reactions, chemical conversion of one or more sites on the 5,7-diene-containing steroid may be effected while the molecule is protected in the form of the Diels-Alder adduct. For example, the $\Delta^{24}$ double bond may be converted to a 24-amino-25-hydroxyl species, a 24,25-dihydroxyl species, or the like. Also, the "A" ring of the steroid may be oxidized when the compound is in adduct form. Examples of chemical conversions which may be carried out on the Diels-Alder adduct are described in co-pending patent application Ser. No. 07/869,328 incorporated by reference above.

It should also be pointed out that a number of the Diels-Alder adducts described hereinabove generically represented by structural formula (XIX) above and include the following specific adducts:

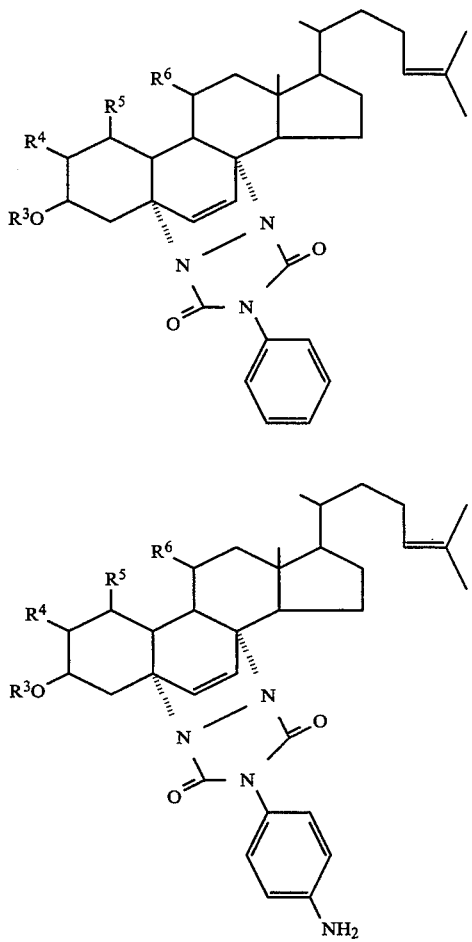

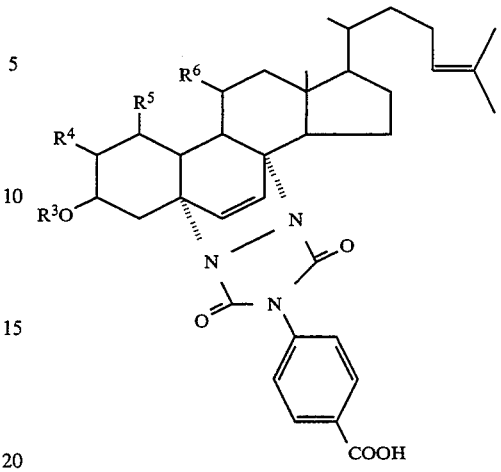

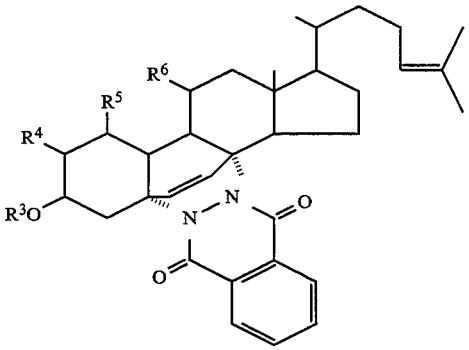

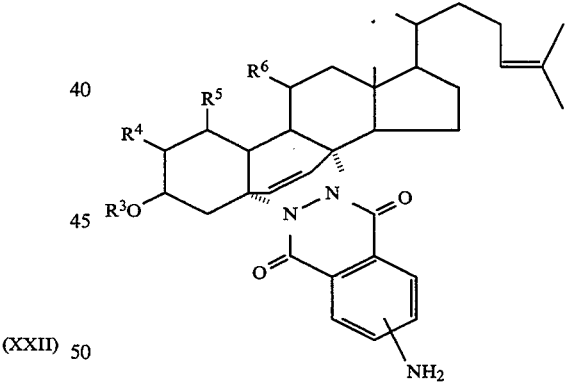

-continued

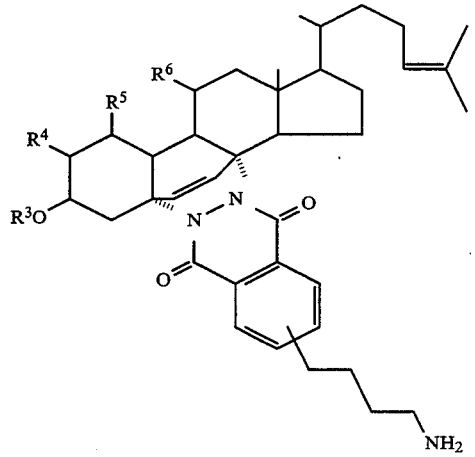

(XXVII)

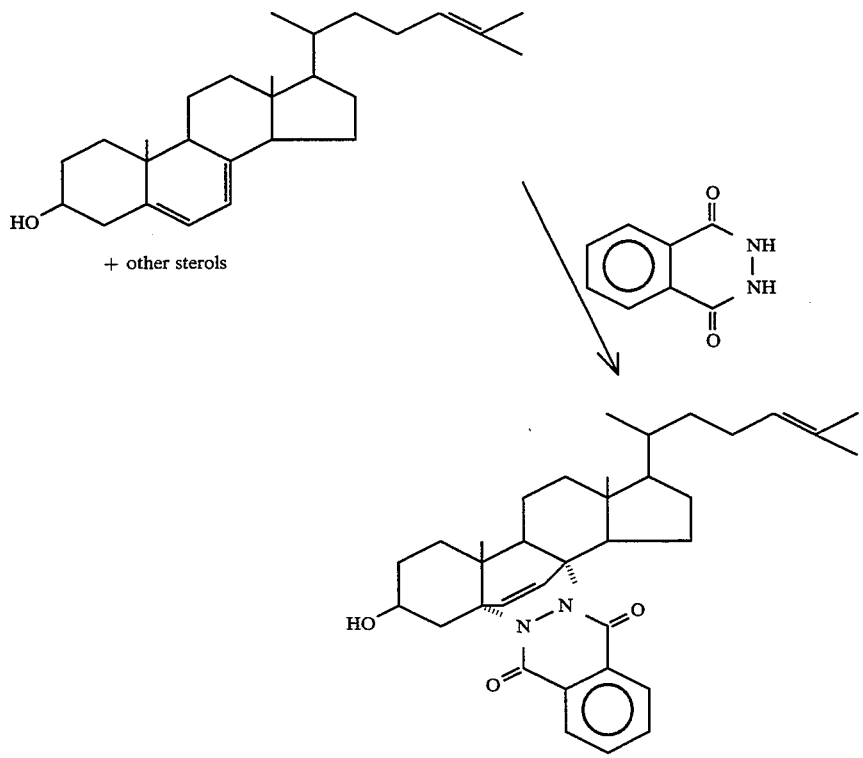

(XXVIII)

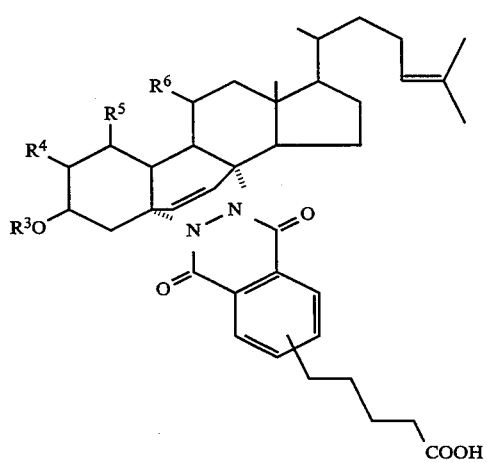

The advantages of the invention include the following: selectivity of reaction of the 5,7-diene-containing steroid with a reactive dienophile; crystallinity of the Diels-Alder adduct, which readily enables removal from the initial sterol mixture; very high yield of the final purified product, on the order of or higher; simplicity of "scaling up" to a manufacturing context; and the ability to modify the 5,7-diene in Diels-Alder adduct form.

It is to be understood that while the invention has been described in conjunction with preferred specific embodiments thereof, the foregoing description, as well as the examples which follow, are intended to illustrate and not limit the scope of the invention. Other aspects, advantages and modifications within the scope of the invention will be apparent to those skilled in the art to which the invention pertains.

EXAMPLE 1

Example 1(a)

To a stirred solution under argon of a crude sterol mixture (obtained from Amoco; 50 g) containing squalene, lanosterol, 4,4-dimethylzymosterol, 4-methylzymosterol, zymosterol, cholesta-7,24-diene-3β-ol and cholesta-5,7,24-triene-3β-ol (11.0 g, pure trienol, 28.8 mmol) dissolved in dichloromethane (600 ml) was added phthalhydrazide (obtained from Aldrich; 15.0 g, 92.5 mmol). This solution was cooled in an ice/water bath (0°–5° C.). To the cooled solution was added dropwise a solution of lead tetraacetate (15.0 g, 33.9 mmol) and acetic acid (1.95 ml) in dichloromethane (215 ml). Addition time 30 min. After stirring at 0°–5° C. for 1.5 hr, the reaction mixture was stirred at room temperature for a total of 4 hr. TLC on silica gel impregnated with silver nitrate showed no trienol present. The reaction mixture was filtered through celite and the combined dichloromethane solution was washed with water and sodium bicarbonate, and again with water. Evaporation of the solvent gave a yellow crude product that was purified in the following way. The crude product was dissolved in a mixture of ethyl acetate and 20% hexane, and filtered through silica gel (125 g). After all the non-reacted sterols had been washed off the column, the adduct was eluted with 50% ethyl acetate in hexane. The yield of pure adduct was 14.1 g, or 90.4%. NMR, IR and mass. spec. were in agreement with the proposed structure.

EXAMPLE 1(b)

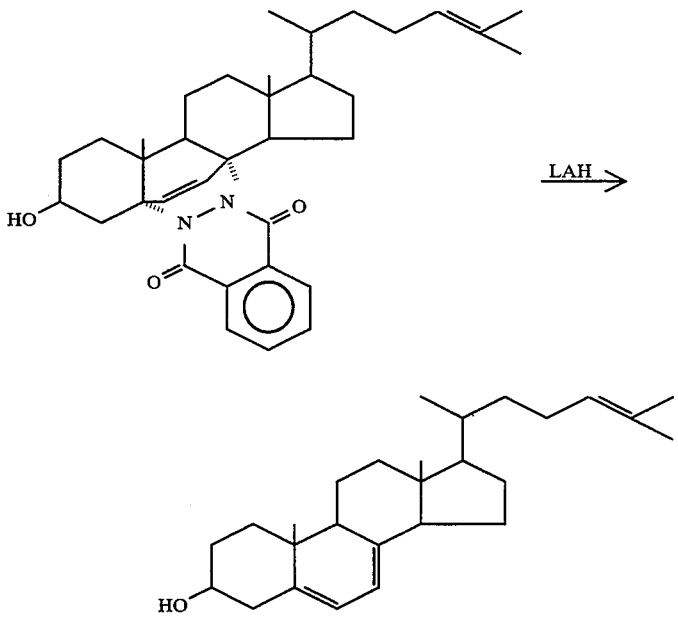

To a solution of the Diels-Alder adduct prepared in the previous section (13.9 g, 25.6 mmol) dissolved in THF (300 ml) and cooled to 0°-5° C. was added dropwise 1M lithium aluminum hydride (LAH) in THF (80 ml, 0 mmol). After stirring at (0°-5° C.) for 1 h, the reaction mixture was warmed to 60° C. for 20 min. The mixture was then cooled to 0°-5° C. and a saturated ammonium chloride solution was added dropwise until excess LAH was destroyed (~20 ml). The reaction mixture was stirred for 30 min and subsequently was left to rest for 30 min. The reaction mixture was then filtered through celite to remove aluminum and lithium salts. The clear THF solution was evaporated to give the crude trienol as a thick yellow syrup. The crude material was recrystallized from methanol to give a total of 7.3 g (74.5%) of pure cholesta-5,7,24-triene-3$\beta$-ol. MP 114°–117° C. NMR, IR, and Mass spectra were in accordance with the proposed structure.

EXAMPLE 2

The procedure of Examples 1(a) and 1(b) may be repeated, except that the phthalhydrazide contains an —$NH_2$ substituent at the 3-position of the phenyl ring (as may be obtained from Aldrich Chemical Co.). The Diels-Alder adduct so provided may be easily separated using acid extraction from the remaining neutral sterols.

EXAMPLE 3

The procedure of Examples 1(a) and 1(b) may be repeated, except that the phthalhydrazide contains an —$NH_2$ substituent at the 4-position of the phenyl ring (as may be obtained from Aldrich Chemical Co.). The Diels-Alder adduct so provided may be easily separated using basic extraction from the remaining neutral sterols.

EXAMPLE 4

The procedure of Examples 1(a) and 1(b) may be repeated, except that 4-phenyl-1,2,4-triazoline-3,5-dione (e.g., as may be obtained from Aldrich Chemical Co.) is substituted for phthalhydrazide and no oxidizing agent is needed or used.

We claim:

1. A method of isolating a sterol containing a 5,7-diene functionality from a mixture of yeast sterol metabolites comprising squalene, lanosterol, 4,4-dimethylzymosterol, 4-methylzymosterol, zymosterol, cholesta-7,24-diene-3-ol and cholesta-5,7,24-triene-3-ol, comprising the steps of: (a) treating said mixture with (i) a dienophile having the structural formula X—R=R—Y wherein the R's are both N or both C—Q where the Q's are H or together from a third bond, and wherein X and Y are selected from electron-withdrawing groups themselves independently selected from the group consisting of —COOH, —CHO, —$NO_2$, —CN, —$COOR^1$ and —$COR^1$ where $R^1$ is lower alkyl, or wherein X and Y are linked together to form a —(CO)—Z—(CO)— bridge in which Z is lower alkylene, monocyclic arylene of 5 to 7 carbon atoms with up to 4 ring substituents, or —$NR^2$— wherein $R^2$ is H, lower alkyl or monocyclic aryl of 5 to 7 carbon atoms and up to 5 ring substituents, wherein the ring substituents are selected from the group consisting of —$(CH_2)_n$—$NH_2$, —$(CH_2)_n$—COOH, —$NO_2$, halogen and lower alkyl, where n is an integer in the range of 0 to 6 inclusive, thereby converting the sterol containing the 5,7-diene functionality to a Diels-Alder adduct; (b) optionally conducting further chemical conversion of the Diels-Alder adduct to provide a modified Diels-Alder adduct; and (c) removing the Diels-Alder adduct or the modified Diels-Alder adduct from the mixture, wherein the 5,7-diene-containing sterol has the structural formula

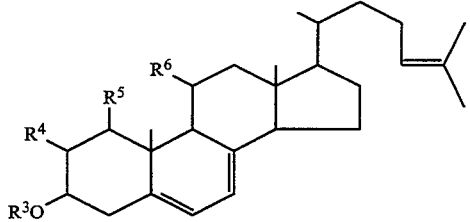

wherein $R^3$ is selected from the group consisting of H and $R^1CO$— wherein $R^1$ is lower alkyl or monocyclic aryl of 5 to 7 carbon atoms, and $R^4$, $R^5$ and $R^6$ are independently selected from the group consisting of H, hydroxyl and lower alkyl.

2. The method of claim 1, wherein the R's of the dienophile are both N, X and Y are linked together to form a —(CO)—Z—(CO)— bridge, and Z is —NR²— where $R^2$ is —(CH$_2$)$_n$—COOH substituents.

3. The method of claim 1, wherein the sterol containing a 5,7-diene functionality is cholesta-5,7,24-triene-3β-ol.

4. The method of claim 1, wherein the removing of the Diels-Alder adduct is effected by crystallization.

5. The method of claim 1, wherein the removing of the Diels-Alder adduct is effected by precipitation.

6. The method of claim 1, wherein the removing of the Diels-Alder adduct is effected chromatograhically.

7. A method of isolating a sterol containing a 5,7-diene functionality from a mixture of yeast sterol metabolites comprising squalene, lanosterol, 4,4-dimethylzymosterol, 4-methylzymosterol, zymosterol, cholesta-7,24-diene-3-ol and cholesta-5,7,24-triene-3-ol, comprising the steps of: (a) treating said mixture with (i) a dienophile precursor having the structural formula X—NH—NH—Y wherein X and Y are selected from electron-withdrawing groups themselves independently selected from the group consisting of —COOH, —CHO, —NO$_2$, —CN, —COOR$^1$ and —COR$^1$ where $R^1$ is lower alkyl, or wherein X and Y are linked together to form a —(CO)—Z—(CO)— bridge in which Z is lower alkylene, monocyclic arylene of 5 to 7 carbon atoms with up to 4 ring substituents, or —NR²— wherein $R^2$ is H, lower alkyl or monocyclic aryl of 5 to 7 carbon atoms and up to 5 ring substituents, wherein the ring substituents are selected from the group consisting of —(CH$_2$)$_n$—NH$_2$, —(CH$_2$)$_n$—COOH, —NO$_2$, halogen and lower alkyl, where n is an integer in the range of 0 to 6 inclusive, and (ii) an oxidizing agent effective to oxidize the precursor, thereby converting the sterol containing the 5,7-diene functionality to a Diels-Alder adduct; (b) optionally conducting further chemical conversion of the Diels-Alder adduct to provide a modified Diels-Alder adduct; and (c) removing the Diels-Alder adduct or the modified Diels-Alder adduct from the mixture, wherein the 5,7-diene-containing sterol has the structural formula

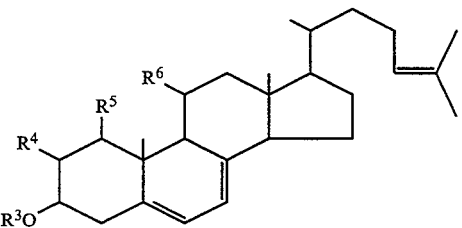

wherein $R^3$ is selected from the group consisting of H and $R^1CO$— where $R^1$ is lower alkyl or monocyclic aryl of 5 to 7 carbon atoms, and $R^4$, $R^5$ and $R^6$ are independently selected from the group consisting of H, hydroxyl and lower alkyl.

8. The method of claim 7, wherein in the dienophile precursor X and Y are linked together to form a —(CO)—Z—(CO)— bridge, and Z is monocyclic arylene of 5 to 7 carbon atoms substituted with up to 2 substituents selected from the group consisting of —(CH$_2$)$_n$—NH$_2$ and —(CH$_2$)$_n$—COOH.

9. The method of claim 8, wherein the dienophile is phthalhydrazide.

10. The method of claim 7, wherein the sterol containing a 5,7-diene functionality is cholesta-5,7,24-triene-3β-ol.

11. The method of claim 7, wherein the removing of the Diels-Alder adduct is effected by crystallization.

12. The method of claim 7, wherein the removing of the Diels-Alder adduct is effected by precipitation.

13. The method of claim 7, wherein the removing of the Diels-Alder adduct is effected chromatographically.

14. The method of claim 7, wherein the oxidizing agent is selected from the group consisting of potassium peroxymonosulfate, lead tetraacetate, iodosobenzene diacetate, N-bromosuccinimide and t-butyl hypochlorite.

15. The method of claim 14, wherein the oxidizing agent is lead tetraacetate.

16. A method of isolating cholesta-5,7,24-triene-3β-ol from a mixture of yeast sterol metabolites comprising squalene, lanosterol, 4,4-dimethylzymosterol, 4-methylzymosterol, zymosterol, cholesta-7,24-diene-3β-ol and cholesta-5,7,24-triene-3β-ol, wherein the method comprises: (a) treating said mixture with phthalhydrazide and lead tetraacetate in an amount effective to oxidize the phthalhydrazide, thereby converting the cholesta-5,7,24-triene-3β-ol in the mixture to a Diels-Alder adduct; (b) applying the reaction mixture of step (a) to a silica gel column and eluting with a solvent system effective to remove all components of the reaction mixture from the column except for the Diels-Alder adduct; (c) removing the Diels-Alder adduct from the column; and (d) treating the Diels-Alder adduct with lithium aluminum hydride, to cleave the adduct and regenerate the cholesta-5,7,24-triene-3β-ol in isolated form.

17. A method of isolating a sterol containing a 5,7-diene functionality from a mixture of yeast sterol metabolites comprising squalene, lanosterol, 4,4-dimethylzymosterol, 4-methylzymosterol, zymosterol, cholesta-7,24-diene-3-ol and cholesta-5,7,24-triene-3-ol, comprising the steps of: (a) treating said mixture with (i) a dienophile having the structural formula X—R=R—Y wherein the R's are both N or both C—Q where the Q's are H or together from a third bond, and wherein X and Y are selected from electron-withdrawing groups themselves independently selected from the group consisting of —COOH, —CHO, —NO$_2$, —CN, —COOR$^1$ and —COR$^1$ where R$^1$ is lower alkyl, or wherein X and Y are linked together to form a —(CO)—Z—(CO)— bridge in which Z is lower alkylene, monocyclic arylene of 5 to 7 carbon atoms and up to 4 ring substituents, or —NR$^2$— wherein R$^2$ is H, lower alkyl or monocyclic aryl of 5 to 7 carbon atoms and up to 5 ring substituents, wherein the ring substituents are selected from the group consisting of —(CH$_2$)$_n$'NH$_2$, —(CH$_2$)$_n$—COOH, —NO$_2$, halogen and lower alkyl, where n is an integer in the range of 0 to 6 inclusive, thereby converting the sterol containing the 5,7-diene functionality to a Diels-Alder adduct; (b) removing the Diels-Alder adduct from the mixture using crystallization, precipitation or chromatography; and (c) treating the Diels-Alder adduct with a reducing agent effective to cleave the adduct and regenerate the 5,7-diene-containing sterol, wherein the 5,7-diene-containing sterol has the structural formula

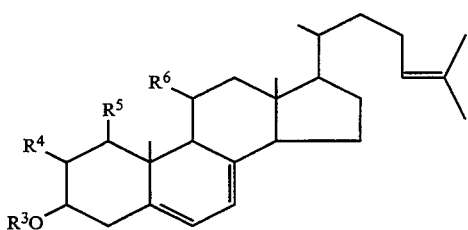

wherein R$^3$ is selected from the group consisting of H and R$^1$CO— where R$^1$ is lower alkyl or monocyclic aryl of 5 to 7 carbon atoms, and R$^4$, R$^5$ and R$^6$ are independently selected from the group consisting of H, hydroxyl and lower alkyl.

18. The method of claim 17, wherein said removing is effected using crystallization.

19. The method of claim 17, wherein said removing is effected using precipitation.

20. The method of claim 17, wherein said removing is effected using chromatography.

21. A method of isolating a sterol containing a 5,7-diene functionality from a mixture of yeast sterol metabolites comprising squalene, lanosterol, 4,4-dimethylzymosterol, 4-methylzymosterol, zymosterol, cholesta-7,24-diene-3-ol and cholesta-5,7,24-triene-3-ol, comprising the steps of: (a) treating said mixture with (i) a dienophile precursor having the structural formula X—NH—NH—Y wherein X and Y are selected from electron-withdrawing groups themselves independently selected from the group consisting of —COOH, —CHO, —NO$_2$, —CN, —COOR$^1$ and —COR$^1$ where R$^1$ is lower alkyl, or wherein X and Y are linked together to form a —(CO)—Z—(CO)— bridge in which Z is lower alkylene, monocyclic arylene of 5 to 7 carbon atoms with up to 4 ring substituents, or —NR$^2$— wherein R$^2$ is H, lower alkyl or monocyclic aryl of 5 to 7 carbon atoms and up to 5 ring substituents, wherein the ring substituents are selected from the group consisting of —(CH$_2$)$_n$—NH$_2$, —(CH$_2$)$_n$—COOH, —NO$_2$, halogen and lower alkyl, where n is an integer in the range of 0 to 6 inclusive, and (ii) an oxidizing agent effective to oxidize the precursor, thereby converting the sterol containing the 5,7-diene functionality to a Diels-Alder adduct; (b) removing the Diels-Alder adduct from the mixture using crystallization, precipitation or chromatography; an (c) treating the Diels-Alder adduct with a reducing agent effective to cleave the adduct and regenerate the 5,7-diene-containing sterol, wherein the 5,7-diene-containing sterol has the structural formula

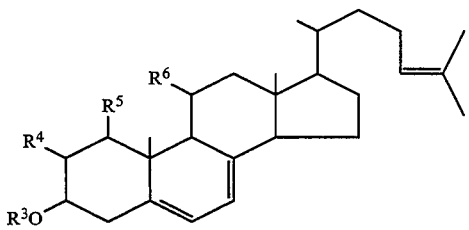

wherein R$^3$ is selected from the group consisting of H and R$^1$CO— where R$^1$ is lower alkyl or monocyclic aryl of 5 to 7 carbon atoms, and R$^4$, R$^5$ and R$^6$ are independently selected from the group consisting of H, hydroxyl and lower alkyl.

22. The method of claim 21, wherein said removing is effected using crystallization.

23. The method of claim 21, wherein said removing is effected using precipitation.

24. The method of claim 21, wherein said removing is effected using chromatography.

* * * * *